United States Patent [19]

Vinci guerra et al.

[11] Patent Number: 5,718,500
[45] Date of Patent: Feb. 17, 1998

[54] POSITIVE PRESSURE IMPACT RESISTANT LENS FOR IMPROVED VISION AND SAFETY

[76] Inventors: Mark T. Vinci guerra, 405 Cypress Dr. #10, Tequestal, Fla. 33469; Jeremiah J. Dooley, 928 Pompano Dr., Jupiter, Fla. 33458

[21] Appl. No.: 535,461

[22] Filed: Sep. 23, 1995

[51] Int. Cl.⁶ .................................. A61F 9/02
[52] U.S. Cl. .................................. 2/431; 2/171.3
[58] Field of Search .................... 2/431, 433, 436, 2/437, 424, 171.3, 8, 9; 62/259.3

[56] References Cited

U.S. PATENT DOCUMENTS

| | | | |
|---|---|---|---|
| 897,290 | 9/1908 | Jacobs | 2/433 |
| 1,464,883 | 8/1923 | Phillips et al. | 2/424 X |
| 2,539,284 | 1/1951 | Thomas | 2/436 |
| 2,654,090 | 10/1953 | Christensen et al. | 2/436 |
| 3,467,965 | 9/1969 | Murphy | 2/171.3 X |

FOREIGN PATENT DOCUMENTS

| | | | |
|---|---|---|---|
| 133723 | 8/1947 | Australia | 2/433 |
| 49105 | 7/1911 | Austria | 2/431 |

*Primary Examiner*—Peter Nerbun
*Attorney, Agent, or Firm*—Gregory J. Gore

[57] ABSTRACT

An impact resistant positive pressure lens is utilized in conjunction with safety goggles or incorporated in a full face mask with a breathing apparatus. The lens protects the wearer from being struck by foreign objects as well as keeping paint over spray, chemicals, grindings and airborne particulate material form adhering to the surface of the lens. The lens consists of a first lens integrally formed with an air inlet chamber to effect an air flow through and out a second lens that is provided with air nozzles. The air nozzles direct the flow of air forward of the second lens and a point at the forward most edge of the shroud, thereby, peventing paint overspray, chemicals, grindings and airborne particulate material from adhering to the second lens.

18 Claims, 3 Drawing Sheets

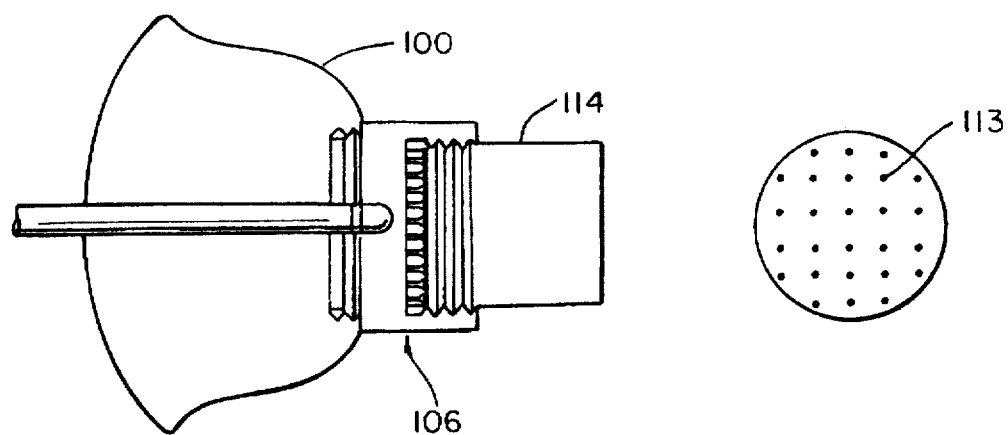
FIG. 1
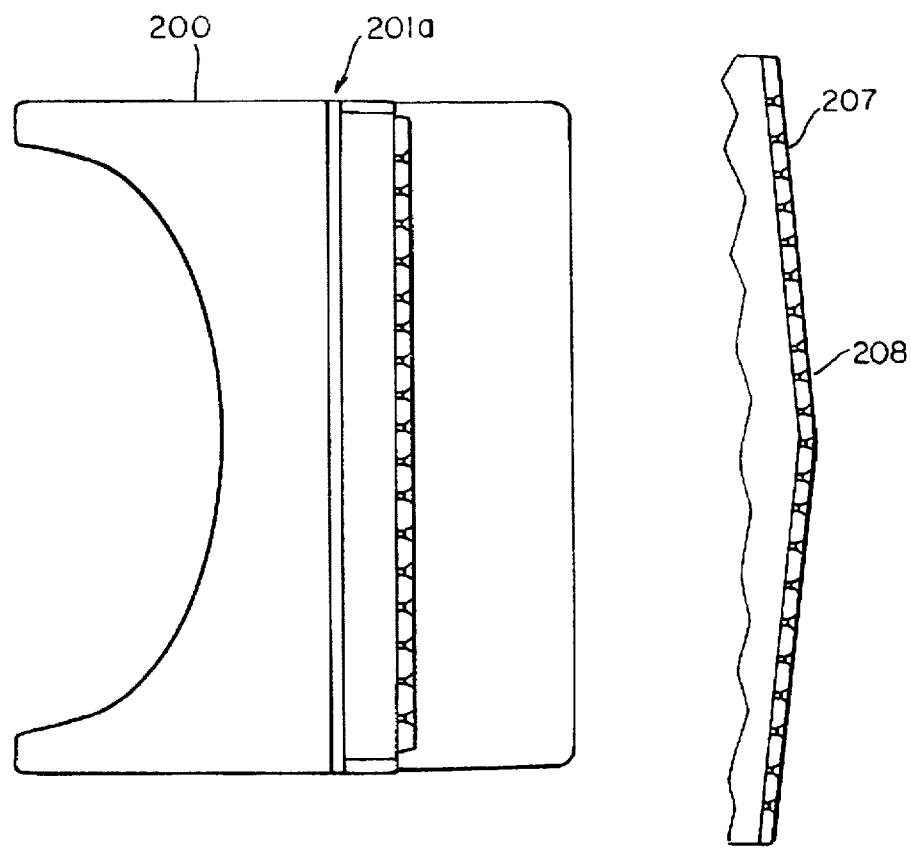
FIG. 3
FIG. 5

POSITIVE PRESSURE IMPACT RESISTANT LENS FOR IMPROVED VISION AND SAFETY

BACKGROUND OF THE INVENTION

1. Field of the Invention

This invention relates to an improved positive or high pressure impact resistant lens to prevent paint overspray, chemicals, grindings and airborne particulate material from adhering to the lens. More particularly, a lens that consists of a positive pressure chamber and a second lens provided with a plurality of air nozzles that are surrounded by a shroud creates an area of high pressure on the outside surface of said second lens therefore, preventing paint over spray, chemicals, grindings and airborne particulate material from adhering to said lens.

2. Description of the Prior Art

Conventional goggles, face masks or spray helmets have a major disadvantage in that paint, chemicals, grindings, and airborne particulate materials have a tendency to adhere to the goggles and the lens. Thus the mask or face shield must be discarded or cleaned periodically. In addition, layers of plastic sheets must be removed and discarded when materials come in contact with plastic lens material. It has been recognized that it is desirable to keep paint, chemicals, grindings and airborne particulate materials from the lens or face mask of protective goggles or protective apparatus. Examples of the prior art are found in the following U.S. Pat. Nos. 1,464,883; 1,960,544 2,818,859; 4,011,865.

U.S. Pat. No. 1,464,883 issued to Phillips has an air ring encircling the viewing lens. It has two distinct disadvantages in that air exiting the ring diffuses immediately rendering the device ineffective. Furthermore, air being pushed across the lens would have the tendency to mix with airborne material allowing the material to adhere to the lens of the device.

In addition, U.S. Pat. No. 4,011,865 discloses a transparent viewing member and viewing opening allowing air on the inside of the mask to blow out through the clearance. It has two distinct disadvantages in that high pressure air utilized to keep particles from adhering to the lens drys the eyes of the user. In addition, air exiting the lens diffuses immediately rendering the device ineffective.

Therefore, there exists a need for a safety lens with an improved air chamber configuration which provides constant air pressure to a second lens that is provided with a plurality of nozzles. The nozzles of the second lens directing the flow of air forward and away from the said second lens in conjunction with an air shroud that maintains an area of positive pressure on the surface of the second lens at a point beyond the forward edge of the said shroud.

SUMMARY OF THE INVENTION

An improved impact resistant positive or high pressure lens provided with a first lens, air inlet apertures, an air chamber, a second lens provided with a plurality of air nozzles and in conjunction with an exterior shroud to provide constant positive pressure beyond the forward edge of the shroud to prevent paint overspray, chemicals, grindings and airborne particulate material from adhering to the positive or high pressure second lens.

The device itself is comprised of synthetic, rubber or plastic material. Furthermore, the device consists of the first lens that protects the user from being struck by foreign objects and serves as an interior portion of the air chamber. Molded, threaded, or held in place by a groove or retainer clip, is the removable second lens provided with a plurality of air nozzles which serves to guide air under pressure to the exterior surface of the lens so that air under pressure is continually pushing away from the lens, creating an area of high pressure on the surface of the lens. It should be noted that the sizes of the air nozzle orifice diameter and nozzle configuration are essential to the operation of the device. In addition, the second lens serves as the first safety barrier to incoming objects projected at the user. Therefore, a double pane barrier is created. Molded, threaded, or snapped to the air chamber exterior surface is the air shroud which serves to maintain an area of high pressure on the surface of the second lens as well as a point beyond of at the edge of the shroud. It should be noted that the length of the shroud, extending away from the second lens, in conjunction with the orifice diameter of the air nozzle and the nozzle configuration are critical to the performance of the device.

In operation the impact resistant positive pressure lens at fed air under pressure from a compressed air source by air inlet apertures on either side of the air chamber. Air under pressure is pushed out a second lens that is provided with a plurlty of air nozzles which direct air away from the lens at an angle incident to incoming airborne particulate material. Air exiting the second lens is kept from diffusion by an air shroud, that surrounds the perimeter of the second lens, which serves to maintain an area of positive or high pressure on the exterior surface of the second lens and a point beyond the forward most edge of the shroud. Therefore, paint over spray, chemicals, grindings and airborne particulate material is kept from adhering to the said second lens.

More specifically, the applicant has invented goggles for eye protection, comprising: a goggle body for mounting on the head of a wearer in front of the eyes; a first lens made of clear material with means for mounting to goggle body; a second lens mounted on the goggle body directly in front of the first lens; an air chamber located between the first lens and the second lens extending substantially across the entire rear surface of the second lens; inlet ports located through right and left lateral sides of the goggle body, the ports being in fluid communication with th air chamber to provide the air chamber with air under pressure; a plurality of air nozzles integrally formed in the second lens, the nozzles being aperatures extending in the front-to-rear direction and providing fluid communication between the air chamber and the area directly in front of the second lens; and a supply of compressed air in fluid communication with the inlet ports, whereby air is directed under pressure through the second lens in the forward direction for creating an area of high pressure along the outside surface of the second lens. The goggles further include an air shroud integrally formed with the goggle body. The air shroud surrounds the perimeter of the second lens to direct the flow of air away from the second lens, maintaining an area of positive pressure on the surface of the second lens at a forward edge of the shroud. The second lens is mounted to the goggles by an expander ring located on opposite sides of the second lens or by inserting the second lens in a slot provided in the top of the goggle. The first lens is attached to the goggle body by inserting the peripheral edges of the first lens into a molded groove located along the inner surface of the goggle body. The air nozzles of the goggles are cone-shaped and cylindrical with a helical groove along their inside surface.

It is therefore an object of the invention to provide a simple means that will permit air to flow away from a lens for creating an area of positive or high pressure on and around the second lens, keeping paint over spray, chemicals, grindings and airborne particulate material from adhering to lens.

Another object of the invention is to provide a double pane safety lens that will resist a great impact and provide additional protection to the wearer.

Still another object of the invention is to provide a removable second lens to facilitate cleaning or disposal.

Another object of the invention is to provide a goggle with interchangeable second lens configurations to compensate for dense or lite particle conditions.

Yet another object of the invention is to provide a second lens with different air nozzle configurations.

Another object of the invention is to provide a second lens with different size air nozzle orifices.

Another object of the invention is to provide a positive or high pressure lens to be used in conjunction with goggles, full face mask and full face mask with breathing apparatus.

BRIEF DESCRIPTION OF THE DRAWINGS

FIG. 1 is a side view of the goggles, air supply line, air inlet aperture, lens, air chamber, air nozzle lens and shroud assembly.

FIG. 3 is a top elevational cross-sectional view of a one piece goggle and molded lens.

FIG. 5 is a lens having a plurality of air nozzles formed therein.

PREFERRED EMBODIMENT OF THE INVENTION

Figure 2:
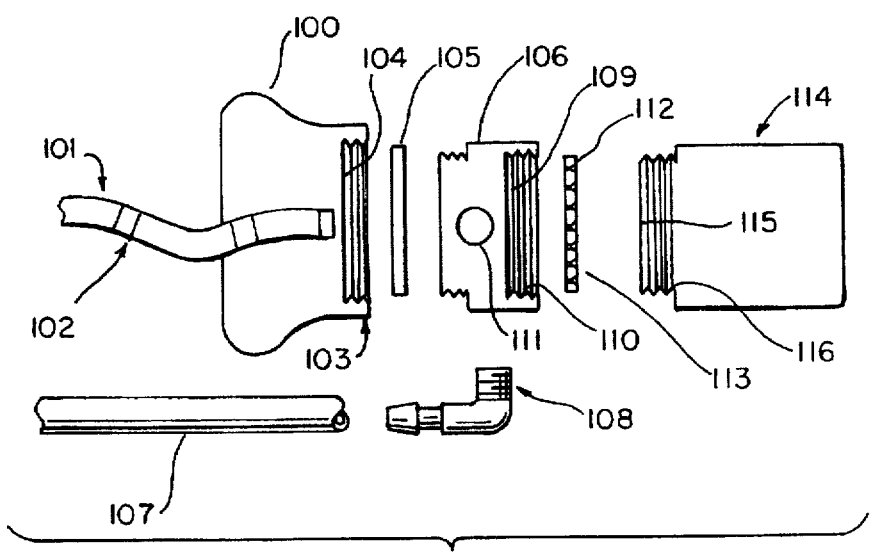
FIG. 2 is a side exploded view of the goggles, strap, air supply line, air inlet aperture, lens, air chamber, air nozzle lens or disc, and shroud.

Referring now to the drawings, and in particular FIGS. 1 and 2, a goggle (100) made of a clear plastic, rubber or synthetic material. An adjustable strap (101) is provided with Velcro band (102) to secure air supply lines thereto. The threaded portion (103) of the goggle includes a first lens seat (104) to allow manual connection of lens (105) and air chamber fixture (106) to goggle (100). An air supply line (107) is connected to air fitting (108) threaded into an air chamber (106) to allow manual connection thereto. The air chamber (106) includes a second lens seat (109), threaded end (110), and a threaded air inlet aperture (111). A second lens (112) includes a plurality of air nozzles (113). An air shroud (114) includes a flat edge (115) and threaded end (116).

Figure 4:
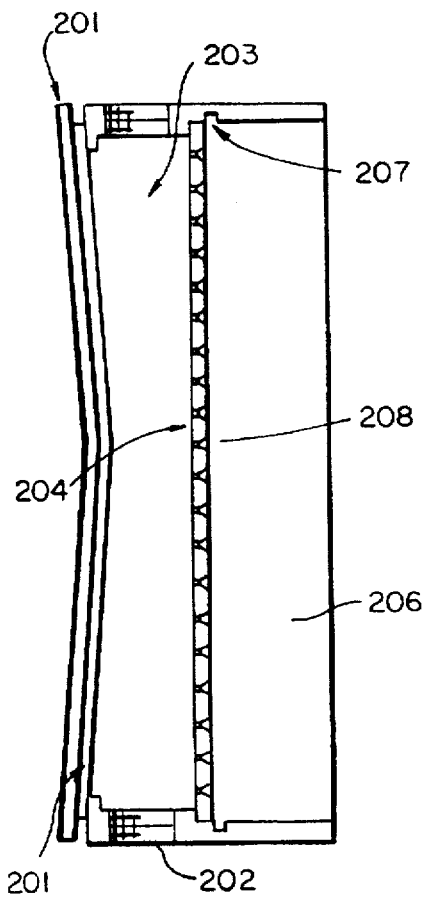
FIG. 4 is an air chamber having an integrally formed lens seat and an air shroud.

Referring to FIGS. 3, 4, 5, an alternate embodiment is shown. A goggle (200) is connected to a one piece molded lens (201a) with groove means (201b) for mounting said lens to the goggle. An air inlet aperture (202) is threaded to allow for manual connection. Air chamber (203) includes an integrally formed lens seat (204) and a molded retainer ring groove (205). An air shroud (206) includes an integrally molded retainer ring groove (205) to secure a second lens (207) having a plurality of air nozzles (208).

Figure 6:
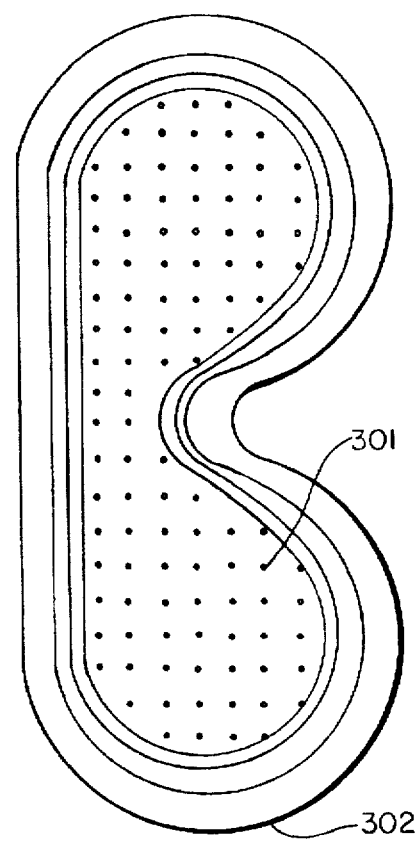
FIG. 6 is a front elevational cross-sectional view of the lens.
Figure 7:
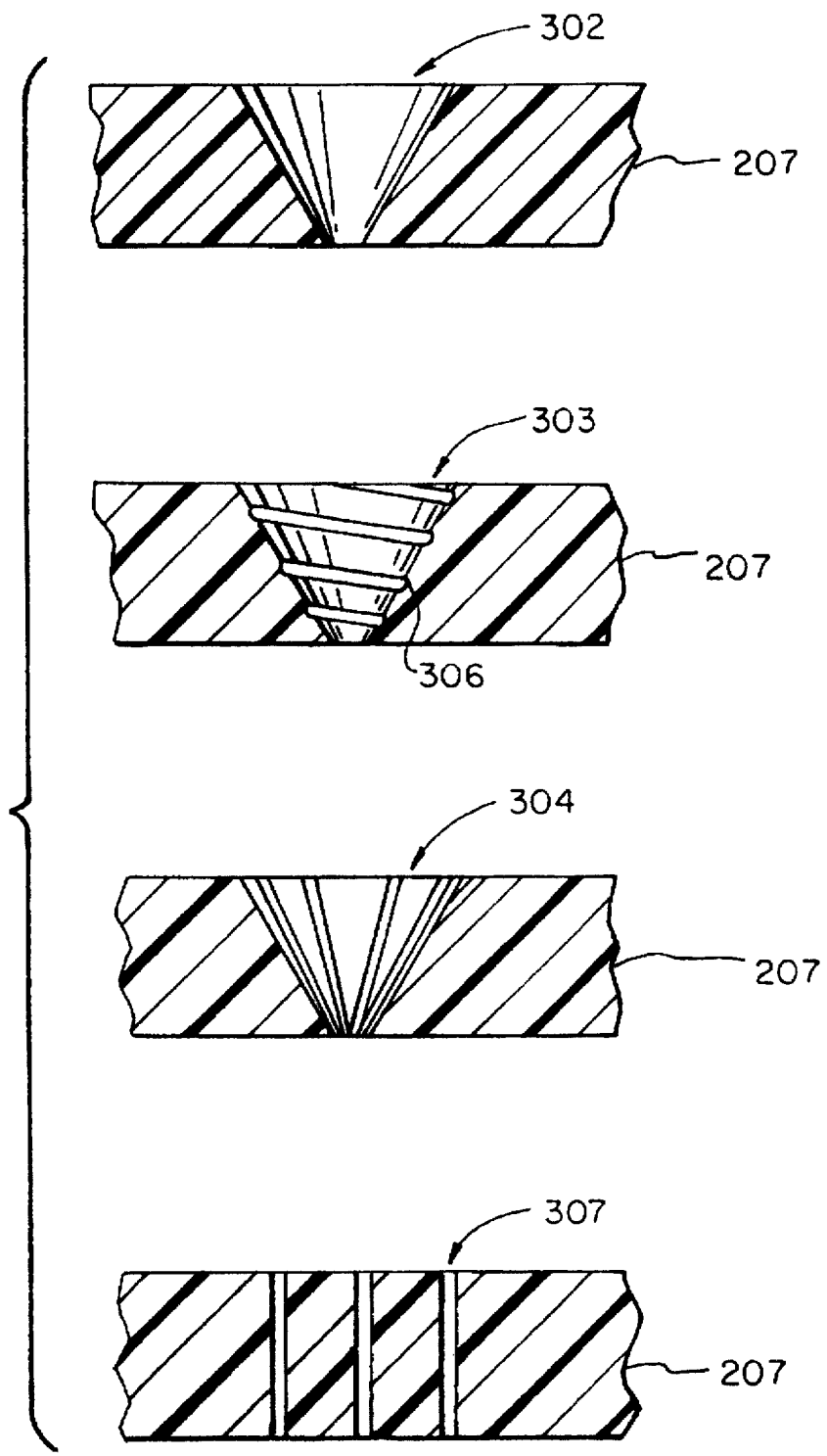
FIG. 7 is a side elevational cross-sectional view of the second lens and air nozzles.

Referring to FIGS. 6 and 7, a second lens (207) is provided with a plurality of air nozzles (301). The second lens (207) contains cone shape nozzles in a binocular configuration (302). In FIG. 7, different nozzle configurations (302), (303), (304) and (307) are shown. Nozzle (303) includes helical grooves (306).

What is claimed is:

1. An impact resistant positive pressure safety lens for use in conjunction with a goggle, full face mask or hood to prevent the wearer from being struck in the eyes from a foreign object and keep paint over spray, chemicals, grindings, and airborne particulate material from adhering to the lens, comprising:

a first lens made of a clear material with edge means for mounting to said goggle;

an air inlet chamber member located behind said first lens extending substantially across the entire rear surface of said lens;

air inlet apertures located on both sides of said air inlet chamber to provide said air chamber with air under pressure; and a second lens, including air nozzle apertures integrated into said second lens to direct air under pressure away from said second lens and to create an area of high pressure on and around the outside surface of said second lens.

2. Goggles for eye protection, comprising:

a goggle body for mounting on the head of a wearer in front of the eyes;

a first lens made of clear material with means for mounting to said goggle body;

a second lens mounted on said goggle body directly in front of said first lens;

an air chamber located between said first lens and said second lens extending substantially across the entire rear surface of said second lens;

inlet ports located through the right and left lateral sides of said goggle body, said ports being in fluid communication with said air chamber to provide said air chamber with air under pressure;

a plurality of air nozzles integrally formed in said second lens, said nozzles being apertures providing fluid communication between said air chamber and the area directly in front of said second lens; and a supply of compressed air in fluid communication with said inlet ports, whereby air is directed under pressure through said second lens in the forward direction.

3. A safety lens according to claim 1 wherein said air chamber and said first and second lens provide a binocular configuration.

4. A safety lens according to claim 1 where said first lens and said second lens are interchangeable to compensate for low or high density airborne particulate material.

5. A safety lens according to claim 1 where a positive pressure lens is secured in place by an expander ring on either side of said second lens.

6. A safety lens according to claim 1 where a positive pressure lens is attached to a goggle or mask by inserting the lens edge into a molded groove in the goggle.

7. A safety lens according to claim 1 where the lens elements are annular and threaded to allow for attachment of said first lens, said air chamber, said second lens and the air shroud.

8. A safety lens according to claim 1 where air is fed into the air chamber by a plastic, vinyl, synthetic rubber or latex air line.

9. A safety lens according to claim 1 where air is fed into the air chamber by an integrally formed air supply line.

10. The goggles of claim 2, further including an air shroud integrally formed with said goggle body, said air shroud surrounding the perimeter of said second lens to direct the flow of air away from said second lens and to maintain an area of positive pressure on the surface of said second lens at a forward edge of said shroud.

11. The goggles of claim 2, in that said second lens is mounted to said goggles by an expander ring located on opposite sides of said second lens.

12. The goggles of claim 2, wherein said second lens is mounted to said goggles by inserting the peripheral edge of said lens into a molded groove located between the air chamber and the air shroud and having a slot at the top of said goggles.

13. The goggles of claim 2, wherein said first lens is attached to said goggle body by inserting the peripheral edges of said first lens into a molded groove located along the inner surface of said goggle body.

14. The goggles of claim 2, further described in that said air nozzles are cone-shaped.

15. The goggles of claim 2, wherein said air nozzles are cylindrical.

16. The goggles of claim 2, wherein said air nozzles further include a helical groove along their inside surface.

17. The goggles of claim 2, wherein said second lens is mounted to said goggle body by inserting the peripheral edge of said second lens into a groove integrally molded into said goggle body.

18. A safety lens according to claim 1, further including an air shroud integrally formed with said goggle body, said air shroud surrounding the perimeter of said second lens to direct the flow of air away from said second lens and to maintain an area of positive pressure on the surface of said second lens at a forward edge of said shroud.

* * * * *